United States Patent
Lin et al.

(10) Patent No.: US 6,200,581 B1
(45) Date of Patent: *Mar. 13, 2001

(54) ELASTOMERIC SILICONE TERPOLYMER

(75) Inventors: Zuchen Lin; William James Schulz, Jr., both of Midland; Janet Mary Smith, Bay City, all of MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/299,864

(22) Filed: Apr. 28, 1999

(51) Int. Cl.$^7$ ............................... A61K 6/00; A61K 7/00
(52) U.S. Cl. .................. 424/401; 424/70.1; 424/70.12; 424/76.1; 424/79; 424/61; 424/63; 424/64; 424/65; 424/73; 424/47; 424/402; 424/404; 528/32; 514/937
(58) Field of Search ............... 424/65, 70.1, 70.12, 424/76.1, 79, 61, 63, 64, 73, 47, 402, 404; 524/731, 261, 860; 528/32; 514/937

(56) References Cited

U.S. PATENT DOCUMENTS

| | | | |
|---|---|---|---|
| 4,853,474 | 8/1989 | Bahr | 556/445 |
| 5,136,068 | 8/1992 | Bahr | 556/445 |
| 5,456,906 | * 10/1995 | Powell et al. | 424/66 |
| 5,654,362 | 8/1997 | Schulz | 524/862 |
| 5,811,487 | 9/1998 | Schulz | 524/862 |
| 5,880,210 | 3/1999 | Schulz | 524/371 |
| 5,889,108 | 3/1999 | Zhang | 524/862 |

* cited by examiner

Primary Examiner—Thorman K. Page
Assistant Examiner—Liliana Di Nola-Baron
(74) Attorney, Agent, or Firm—James L. De Cesare

(57) ABSTRACT

Three-dimensional silicone elastomers having both polyether and higher alkyl functionality present in their molecules are in the form of networks of crosslinked linear siloxanes with polyether and olefin containing repeating units. Representative units are $EO_7$ and $EO_{12}$ for the polyether functionality, and $C_{10}$, $C_{12}$, and $C_{18}$ alkyl functionality for the olefin. These gelled molecules are multipurpose type materials, and consequently they are capable of being useful in a variety of multiphased formulations in personal and health care applications.

12 Claims, No Drawings

ELASTOMERIC SILICONE TERPOLYMER

FIELD OF THE INVENTION

This invention is directed to elastomeric polyorganosiloxanes containing four different types of difunctional "D" units $R_2SiO_{2/2}$. In particular, the elastomeric polyorganosiloxanes according to the invention are terpolymers with (i) dimethyl, (ii) higher alkyl, and (iii) polyether containing "D" units, including (iv) crosslinking "D" units.

These elastomeric silicone terpolymers constitute polymeric molecules which are crosslinked together to such an extent that the material gels. The elastomeric gelled material is in the form of a molecular polymeric network which literally consists of tens, hundreds, and even thousands of crosslinking units derived from the $\equiv$SiH containing polysiloxane precursor, between and among the many polymeric molecules themselves.

BACKGROUND OF THE INVENTION

Because the elastomeric silicone terpolymers according to the present invention are polymeric molecules crosslinked together so that the material actually gels, forming a three-dimensional molecular polymeric network consisting of tens, hundreds, and even thousands of crosslinking units between and among the polymeric molecules, the gelled material herein is not the same as the two-dimensional organopolysiloxane-polyoxyalkylenes described in U.S. Pat. No. 4,853,474 (Aug. 1, 1989) and U.S. Pat. No. 5,136,068 (Aug. 4, 1992). Thus, the specific intent and purpose expressed in both U.S. Pat. No. 4,853,474 and U.S. Pat. No. 5,136,068, is to "avoid gelling".

As a consequence, the materials according to the present invention are capable of performing functions beyond those of the organopolysiloxane-polyoxyalkylenes of U.S. Pat. No. 4,853,474 and 5,136,068. For example, the crosslinked three-dimensional gelled elastomeric silicone terpolymeric networks described in this invention can compatibilize organic oils and silicone oils, and they can be used to thicken organic oils and silicone oils.

They can also be used in the preparation of water-in-silicone oil emulsions, as well as in the preparation of diol containing emulsions such as propylene glycol-in-silicone oil emulsions. Additionally, they can be used in the preparation of water-in-organic oil emulsions containing both non-polar and polar oils. In this application, the interfacial tension (IFT) of the polar oil can be as low as 4.8 mN/m. Further, they are capable of solubilizing and entrapping oil-soluble active ingredients such as vitamin A and vitamin E for delivery of these types of active ingredients to a substrate such as human skin. If desired, the crosslinked three-dimensional elastomeric network containing the active ingredient can then be used for preparing a water-in-oil emulsion including the active ingredient.

Finally, these materials can be used to form a (i) water-in-oil-in-water multiple emulsion, or (ii) diol containing emulsions such as propylene glycol-in-oil-in-propylene glycol multiple emulsions. These multiple or triple emulsions can in turn be used for the purpose of delivering to the skin polar actives such as vitamin C, as well as for the delivery of a-hydroxy acids such as glycolic acid, lactic acid, tartaric acid, and citric acid, i.e., fruit acids. In this latter instance, significant benefits can be realized as fruit acids have been alleged to be capable of diminishing fine skin lines and pigmentation spots, as well as stimulating collagen which allows the skin to repair itself.

As used herein, the term diol is intended to include dihydroxy alcohols containing 2–10 carbon atoms such as ethylene glycol, propylene glycol, and trimethylene glycol, for example.

BRIEF SUMMARY OF THE INVENTION

This invention relates to a composition which is an elastomeric silicone terpolymer prepared by reacting (A) an $\equiv$Si—H containing polysiloxane and (B) a mono-alkenyl polyether in the presence of a platinum catalyst until an $\equiv$Si—H containing polysiloxane with polyether groups is formed; reacting (C) the $\equiv$Si—H containing polysiloxane with polyether groups and (D) an $\alpha$-olefin containing at least ten carbon atoms in the presence of a platinum catalyst until an $\equiv$Si—H containing polysiloxane with polyether and alkyl groups containing ten or more carbon atoms is formed; and reacting (E) the $\equiv$Si—H containing polysiloxane with polyether and alkyl groups containing ten or more carbon atoms and (F) an $\alpha,\omega$-unsaturated hydrocarbon such as an $\alpha,\omega$-diene, $\alpha,\omega$-diyne, or an $\alpha,\omega$-ene-yne in the presence of (G) an oil and a platinum catalyst until a silicone elastomer is formed by crosslinking and addition of $\equiv$SiH across double or triple bonds in the $\alpha,\omega$-unsaturated hydrocarbon. The reaction is allowed to continue until there is formed a crosslinked three-dimensional gelled network of an elastomeric silicone terpolymer.

The invention also relates to materials comprising this composition in combination with oil-soluble as well as water-soluble active ingredients.

The invention further relates to emulsions and multiple emulsions containing the composition.

In this regard, it is noted that multiple emulsions are composed of droplets of one liquid dispersed in larger droplets of a second liquid which are then dispersed in a final continuous phase. Generally, the internal droplet phase will be miscible with or identical to the final continuous phase. For example, in a water-in-oil-in-water multiple emulsion W/O/W, the internal and external phases are aqueous.

For a W/O/W system, in which the final continuous phase is aqueous, the primary emulsion is a water-in-oil emulsion W/O, which is then emulsified into the final aqueous phase.

For the purpose of clarity, and according to recognized standards of nomenclature used for W/O/W systems, the aqueous phase of the primary emulsion is designated as $W_1$, and the primary emulsion is designated as $W_1/O$. The primary emulsion $W_1/O$ includes an oil phase which is designated as O. After the primary emulsion $W_1/O$ has been further dispersed in the second aqueous phase designated as $W_2$, the complete multiple emulsion system is designated as $W_1/O/W_2$.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

According to this invention, an elastomeric silicone terpolymer can be prepared and used as generally depicted in one or more of the several processing steps shown below:

Step 1: Incorporation of the Polyether $\equiv$SiH siloxane+mono-alkenyl polyether+Pt catalyst→$\equiv$SiH siloxane with polyether groups Step 1': Incorporation of the α-Olefin

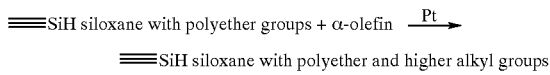

≡SiH siloxane with polyether groups + α-olefin —Pt→

≡SiH siloxane with polyether and higher alkyl groups

Step 2: Gelation
≡SiH siloxane with polyether and higher alkyl groups+
≡SiH siloxane (optional)+α,ω-unsaturated hydrocarbon+oil+Pt catalyst→gel/elastomer
Step 3: Shearing & Swelling—Optional
gel/elastomer+oil+quencher+active ingredient→paste
Step 4: Emulsification/Preparation of Primary Emulsion—Optional
silicone gel/elastomer/paste+$H_2O$+active ingredient+ shear→primary emulsion $W_1$/O
Step 5: Preparation of Multiple Emulsion $W_1$/O/$W_2$— Optional
$W_1$/O+$H_2O$+shear→$W_1$/O/$W_2$ multiple emulsion In Step 1, the molar ratio of the mono-alkenyl polyether to the ≡SiH in the ≡SiH siloxane should be between 0.9:1 to 1:100. Step 1 and Step 1' can be reversed, in which case, the molar ratio of the α-olefin to the ≡SiH in the ≡SiH siloxane should also be between 0.9:1 to 1:100.

In Step 2, the weight ratio of the oil to the weight of the ≡SiH siloxane with polyether and higher alkyl groups and the α,ω-unsaturated hydrocarbon can be from 1:1 to 98:1, but preferably is between 5:1 to 15:1. The ratio of the ≡SiH in the ≡SiH containing siloxane with polyether and higher alkyl groups and the α,ω-unsaturated hydrocarbon can be from 2:1 to 1:2, but preferably is 1:1.

Many types of compounds can be used to prepare elastomeric silicone terpolymers according to the method shown in Steps 1, 1', and 2, representative of which are;
$HSiMe_2O(Me_2SiO)_{10}SiHMe_2$
$Me_3SiO(Me_2SiO)_8(MeHSiO)_4SiMe_3$
$Me_3SiO(Me_2SiO)_{50}[MeGSiO]_4(MeHSiO)_5SiMe_3$
$Me_3SiO(Me_2SiO)_{50}[MeG'SiO]_4(MeHSiO)_5SiMe_3$
$Me_3SiO(Me_2SiO)_{50}[MeGSiO]_4[MeG'SiO]_4(MeHSiO)_5SiMe_3$, 1,5-hexadiene, and decamethylcyclopentasiloxane.

In these formulas, Me is methyl, G represents the group —$CH_2CH_2CH_2O(CH_2CH_2O)_{10}H$, and G' is a higher alkyl radical containing ten or more carbon atoms, preferably twelve or more carbon atoms, and most preferably sixteen or more carbon atoms.

In optional Step 3, the silicone paste should contain 60–98 percent by weight of the oil. In Steps 4 and 5, the weight ratio of water to the silicone paste can be 95:5 to 5:95.

If desired, post cure caused by residual crosslinking hydrosilylation reactions occurring in silicone elastomers can be terminated by introducing an ≡SiH quenching agent such as a vinylsiloxane or a vinylsilane. While vinylsiloxanes and/or vinylsilanes can be used to completely terminate post cure, vinylsiloxanes are preferred to react with ≡SiH over other types of alkenylsiloxanes. In the process of making compositions according to the present invention, a vinylsiloxane can be introduced at the shear & swell Step 3. When this is carried out, any on-going reactions of residual functionalities will be shifted to reactions between the incoming vinylsiloxane and the residual ≡SiH, with the result that crosslinking reactions will be terminated.

Representative of some organosilicon compounds and polymers which can be used as quenching agents are silanes such as vinyl-t-butyldimethylsilane, vinyldiethylmethylsilane, vinylethyldimethylsilane, vinyltriethylsilane, vinyltrimethylsilane, divinyldimethylsilane, and divinyltetramethyldisilane; and siloxanes such as vinylpentamethyldisiloxane, 1,3-divinyltetramethyldisiloxane, a vinyltrisiloxane such as $(CH_3)_3SiOSi(CH|CH_2)(CH_3)OSi(CH_3)_3$, 1,5-divinylhexamethyltrisiloxane, and a divinylsiloxane oligomer having an average structure $(CH_2|CH)Me_2SiO(Me_2SiO)_8SiMe_2(CH|CH_2)$.

Other types of quenching agents can also be used such as strong platinum complexing ligands, terminal alkynes, and amino acid esters. Representative ligands include trialkyl and triaryl phosphines such as triphenylphosphine $PPh_3$; amines, diamines, and triamines such as n-butylamine $CH_3(CH_2)_3NH_2$, triethanolamine $(HOCH_2CH_2)_3N$, and tetramethylethylene diamine $(CH_3)_2NCH_2CH_2N(CH_3)_2$; and organic sulfides such as ethyl phenyl sulfide $C_6H_5SC_2H_5$.

Some examples of suitable terminal alkynes which can be used are acetylene, propyne, 1-butyne, 1-pentyne, 4,4-dimethyl-1-pentyne, 1-hexyne, 5-methyl-1-hexyne, and 1-decyne.

In addition, the quenching agent can be an amino acid ester, preferably a sulfur containing amino acid ester, such as methionine methyl ester, methionine ethyl ester, cysteine methyl ester, cysteine ethyl ester, and cystine dimethyl ester.

The feature of using quenching agents to terminate post cure is the subject matter of copending application U.S. Pat. No. 5,928,164, filed Nov. 5, 1997, in the name of Shizhong Zhang, entitled "Quenching Post Cure"; and copending application U.S. Pat. No. 5,977,280, filed Nov. 5, 1997, in the name of Donald A. Kadlec, William J. Schulz, and Shizhong Zhang, entitled "Terminating Post Cure With Amino Acid Esters". Both applications are assigned to the same assignee as the present invention.

The ≡Si—H siloxane in Step 1 is represented by compounds of the formula $R_3SiO(R'_2SiO)_a(R''HSiO)_bSiR_3$, compounds of the formula $HR_2SiO(R'_2SiO)_cSiR_2H$, or compounds of the formula $HR_2SiO(R'_2SiO)_a(R''HSiO)_bSiR_2H$. Mixtures of these types of compounds can also be employed. In the three formulas, R, R', and R", are alkyl groups with 1–6 carbon atoms; a is 0–250; b is 1–250; and c is 0–250.

The ≡Si—H containing polysiloxane can also comprise an alkylhydrogen cyclosiloxane or an alkylhydrogen-dialkyl cyclosiloxane copolymer, represented in general by the formula $(R'_2SiO)_{a'}(R''HSiO)_{b'}$, where R' and R" are as defined above, and where a' is 0–7 and b' is 3–10. Some representative compounds of these types are $(OSiMeH)_4$, $(OSiMeH)_3(OSiMeC_6H_{13})$, $(OSiMeH)_2(OSiMeC_6H_{13})_2$, and $(OSiMeH)(OSiMeC_6H_{13})_3$, where Me represents —$CH_3$.

An α,ω-unsaturated hydrocarbon is used in Step 2, and the most preferred α,ω-unsaturated hydrocarbon is an α,ω-diene of the formula $CH_2=CH(CH_2)_dCH=CH_2$ where d is 1–20. Some representative examples of suitable α,ω-dienes for use herein are 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

However, other α,ω-unsaturated hydrocarbons can be used such as α,ω-diynes of the formula $CH\equiv C(CH_2)_eC\equiv CH$; or α,ω-ene-ynes of the formula $CH_2=CH(CH_2)_eC\equiv CH$ where e is 0–20. Some representative examples of suitable α,ω-diynes for use herein are 1,3-butadiyne $HC\equiv C—C\equiv CH$ and 1,5-hexadiyne (dipropargyl) $HC\equiv C—CH_2CH_2—C\equiv CH$. One example of a suitable α,ω-ene-yne for use herein is hexene-5-yne-1 $CH_2=CHCH_2CH_2C\equiv CH$.

The reactions in Steps 1, 1X, 2 requires a catalyst to effect the reaction between the ≡SiH containing siloxane, the mono-alkenyl polyether, the α-olefin, and the α,ω-unsaturated hydrocarbon. Suitable catalysts are Group VIII transition metals, i.e., the noble metals. Such noble metal catalysts are described in U.S. Pat. No. 3,923,705, incorporated herein by reference. A particularly preferred catalyst is described in Karstedt's U.S. Pat. Nos. 3,715,334 and 3,814,730, incorporated herein by reference. Karstedt's catalyst is a platinum divinyl tetramethyl disiloxane complex, typically containing about one weight percent of platinum, carried in a polydimethylsiloxane fluid or in a solvent such as toluene.

The particular catalyst used in the examples was 20 µl and 200 µl portions of Karstedt's catalyst as one weight percent of platinum carried in a 2.0 mm$^2$/s polydimethylsiloxane fluid. Another preferred platinum catalyst is a reaction product of chloroplatinic acid and an organosilicon compound containing terminal aliphatic unsaturation. It is described in U.S. Pat. No. 3,419,593, incorporated herein by reference. The noble metal catalysts are used in amounts of from 0.00001–0.5 parts per million of noble metal per 100 weight parts of ≡SiH containing polysiloxane, preferably 0.00001–0.02 parts per million of noble metal, most preferably 0.00001–0.002 parts per million of noble metal.

The mono-alkenyl polyether is a compound of the formula $CH_2=CH(CH_2)_fO(CH_2CH_2O)_g(CH_2CH_3CHO)_hT$, or a compound of the formula $CH_2=CH-Q-O(CH_2CH_2O)_g(CH_2CH_3CHO)_hT$. In the formulas, T represents an end group which can be hydrogen; a C1–C10 alkyl group such as methyl, ethyl, propyl, butyl, and decyl; an aryl group such as phenyl; or a C1–C20 acyl group such as acetyl, propionyl, butyryl, lauroyl, myristoyl, and stearoyl. Q is a divalent linking group containing unsaturation such as phenylene $—C_6H_4—$. The value of f is 0–6; g has a value of 4–100; and h can be zero or have a value of 1–100.

It should be noted that when one desires to deliver vitamin A derivatives as an active ingredient, g should referably have a value of at least 7, i.e. 7–100, rather than 4–100.

The α-olefin is a compound of the formula $CH_2=CHR'''$ where R''' is a higher alkyl group containing 8–40 carbon atoms. Some representative examples of suitable α-olefins for use herein are 1-decene ($C_{10}$), 1-undecene, 1-dodecene, 1-tridecene, 1-tetradecene, 1-pentadecene ($C_{15}$), 1-hexadecene, 1-octadecene, 1-nonadecene, 1-eicosene ($C_{20}$), 1-heptacosene, and α-olefin fractions containing various amounts of $C_{22-C30}$+α-olefins sold under the trademark GULFTENE® 24–28 and GULFTENE® 30+ by the Chevron Chemical Company, Houston, Tex.

The term oil as used herein is intended to include compounds containing a silicon atom such as low molecular weight linear and cyclic volatile and non-volatile alkyl and aryl siloxanes, and low molecular weight functional linear and cyclic siloxanes. Most preferred, however, are low molecular weight linear and cyclic volatile methyl siloxanes. Thus, this particular component constitutes what is shown as the "oil" in Step 2 of the process illustrated above.

Volatile methyl siloxanes correspond to the average unit formula $(CH_3)_jSiO_{(4-j)/2}$ in which j has an average value of two to three. The compounds contain siloxane units joined by ≡Si—O—Si≡ bonds. Representative units are monofunctional "M" units $(CH_3)_3SiO_{1/2}$ and difunctional "D" units $(CH_3)_2SiO_{2/2}$.

The presence of trifunctional "T" units $CH_3SiO_{3/2}$ results in the formation of branched linear or cyclic volatile methyl siloxanes. The presence of tetrafunctional "Q" units $SiO_{4/2}$ results in the formation of branched linear or cyclic volatile methyl siloxanes.

Linear volatile methyl siloxanes have the formula $(CH_3)_3SiO\{(CH_3)_2SiO\}_kSi(CH_3)_3$. The value of k is 0–5. Cyclic volatile methyl siloxanes have the formula $\{(CH_3)_2SiO\}_m$. The value of m is 3–9. Preferably, these volatile methyl siloxane have a boiling point less than about 250° C. and viscosity of about 0.65 to about 5.0 mm$^2$/s.

Representative linear volatile methyl siloxanes are hexamethyldisiloxane (MM) with a boiling point of 100° C., viscosity of 0.65 mm$^2$/s and formula $Me_3SiOSiMe_3$; octamethyltrisiloxane (MDM) with a boiling point of 152° C., viscosity of 1.04 mm$^2$/s, and formula $Me_3SiOMe_2SiOSiMe_3$; decamethyltetrasiloxane ($MD_2M$) with a boiling point of 194° C., viscosity of 1.53 mm$^2$/s, and formula $Me_3SiO(Me_2SiO)_2SiMe_3$; dodecamethylpentasiloxane ($MD_3M$) with a boiling point of 229° C., viscosity of 2.06 mm$^2$/s, and formula $Me_3SiO(Me_2SiO)_3SiMe_3$; tetradecamethylhexasiloxane ($MD_4M$) with a boiling point of 245° C., viscosity of 2.63 mm$^2$/s, and formula $Me_3SiO(Me_2SiO)_4SiMe_3$; and hexadecamethylheptasiloxane ($MD_5M$) with a boiling point of 270° C., viscosity of 3.24 mm$^2$/s, and formula $Me_3SiO(Me_2SiO)_5SiMe_3$.

Representative cyclic volatile methyl siloxanes are hexamethylcyclotrisiloxane ($D_3$) a solid with a boiling point of 134° C. and formula $\{(Me_2)SiO\}_3$; octamethylcyclotetrasiloxane ($D_4$) with a boiling point of 176° C., viscosity of 2.3 mm$^2$/s, and formula $\{(Me_2)SiO\}_4$; decamethylcyclopentasiloxane ($D_5$) with a boiling point of 210° C., viscosity of 3.87 mm$^2$/s, and formula $\{(Me_2)SiO\}_5$; and dodecamethylcyclohexasiloxane ($D_6$) with a boiling point of 245° C., viscosity of 6.62 mm$^2$/s, and formula $\{(Me_2)SiO\}_6$.

Representative branched volatile methyl siloxanes are heptamethyl-3-{(trimethylsilyl)oxy}trisiloxane ($M_3T$) with a boiling point of 192° C., viscosity of 1.57 mm$^2$/s, and formula $C_{10}H_{30}O_3Si_4$; hexamethyl-3,3,bis {(trimethylsilyl)oxy} trisiloxane ($M_4Q$) with a boiling point of 222° C., viscosity of 2.86 mm$^2$/s, and formula $C_{12}H_{36}O_4Si_5$; and pentamethyl {(trimethylsilyl)oxy} cyclotrisiloxane ($MD_3$) with the formula $C_8H_{24}O_4Si_4$.

The invention also includes using low molecular weight linear and cyclic non-volatile alkyl and aryl siloxanes represented respectively by the formulas $R^a_3SiO(R^a_2SiO)_nSiR^a_3$ and $(R^a_2SiO)_p$. $R^a$ can be an alkyl group with 1–20 carbon atoms, or an aryl group such as phenyl. The value of n is 0–80, preferably 5–20. The value of p is 3–9, preferably 4–6. These polysiloxanes generally have a viscosity in the range of about 5–100 mm$^2$/s.

Polysiloxanes can also be used where n has a value sufficient to provide siloxane polymers with a viscosity in the range of about 100–1,000 mm$^2$/sec. Typically, n can be about 80–375. Illustrative of such polysiloxanes are polydimethylsiloxane, polydiethylsiloxane, polymethylethylsiloxane, polymethylphenylsiloxane, and polydiphenylsiloxane.

Low molecular weight functional polysiloxanes can also be employed, and are represented by the formula $R^b_3SiO(R^bYSiO)_nSiR^b_3$ where $R^b$ can be alkyl groups with 1–20 carbon atoms or aryl groups such as phenyl, Y is a functional group, and n is 0–80. Examples of such functional polysiloxanes containing functional groups represented by Y are acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, polyisobutylene (PIB) functional siloxane fluids, silanol functional siloxanes, and vinyl functional siloxane fluids.

The invention is not limited to using only low molecular weight siloxanes. Other types of oils can be used in Step 2 of the process. Thus, an oil or mixture of oils may be used.

The term oil is therefore further intended to include (i) organic compounds, (ii) compounds containing a silicon atom as enumerated above, (iii) mixtures of organic compounds, (iv) mixtures of compounds containing a silicon atom, or (v) mixtures of organic compounds and compounds containing a silicon atom; used on an industrial scale to dissolve, suspend, or change the physical properties of other materials.

In general, the organic compounds used as oils are aromatic hydrocarbons, aliphatic hydrocarbons, alcohols, aldehydes, ketones, amines, esters, ethers, glycols, glycol ethers, alkyl halides, or aromatic halides. Representative compounds are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, Varnish Maker's & Painter's (VM&P) solvent, and mineral spirits; alkyl halides such as chloroform, carbon tetrachloride, perchloroethylene, ethyl chloride, and chlorobenzene; aromatic hydrocarbons such as benzene, toluene, ethylbenzene, and xylene; esters such as ethyl acetate, isopropyl acetate, ethyl acetoacetate, amyl acetate, isobutyl isobutyrate, benzyl acetate, and isopropyl palmitate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as petroleum jelly, mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil, and whale oil.

Other miscellaneous organic oils can also be used such as acetonitrile, nitromethane, dimethylformamide, propylene oxide, trioctyl phosphate, butyrolactone, furfural, pine oil, turpentine, and m-cresol.

Further intended to be included in the term oil are volatile flavoring agents such as oil of wintergreen; peppermint oil; spearmint oil; menthol; vanilla; cinnamon oil; clove oil; bay oil; anise oil; eucalyptus oil; thyme oil; cedar leaf oil; oil of nutmeg; oil of sage; cassia oil; cocoa; licorice; high fructose corn syrup; citrus oils such as lemon, orange, lime, and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

In addition, the term oil is intended to include volatile fragrances such as natural products and perfume oils. Some representative natural products and perfume oils are ambergris, benzoin, civet, clove, leaf oil, jasmine, mate', mimosa, musk, myrrh, orris, sandalwood oil, and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

Useful active ingredients for use in Steps 3 and 4 of processes according to the invention include both fat or oil-soluble vitamins as well as water-soluble vitamins. Oil-soluble vitamins useful herein include, but are not limited to, Vitamin $A_1$, RETINOL, $C_2$–$C_{18}$ esters of RETINOL, vitamin E, TOCOPHEROL, esters of vitamin E, and mixtures thereof. RETINOL includes trans-RETINOL, 13-cis-RETINOL, 11-cis-RETINOL, 9-cis-RETINOL, and 3,4-didehydro-RETINOL. The oil-soluble vitamin can be used in the composition according to the invention in amounts of from 0.01 to about 50 percent by weight.

RETINOL, it should be noted, is an International Nomenclature Cosmetic Ingredient Name (INCI) designated by The Cosmetic, Toiletry, and Fragrance Association (CTFA), Washington DC, for vitamin A. Other suitable vitamins and the INCI names for the vitamins considered included herein are RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Water-soluble vitamins useful herein include, but are not limited to, Vitamin C, Vitamin $B_1$, Vitamin $B_2$, Vitamin $B_6$, Vitamin $B_{12}$, niacin, folic acid, biotin, and pantothenic acid. Other suitable water-soluble vitamins and the INCI names for the vitamins considered included herein are ASCORBYL DIPALMITATE, ASCORBYL METHYLSILANOL PECTINATE, ASCORBYL PALMITATE, and ASCORBYL STEARATE. The water-soluble vitamin, like the oil-soluble vitamin, can be used in the composition according to the invention in amounts of from 0.01 to about 50 percent by weight.

Some examples of commercially available products suitable for use herein are Vitamin A Acetate and Vitamin C, both products of Fluka Chemie AG, Buchs, Switzerland; COVI-OX T-50, a vitamin E product of Henkel Corporation, La Grange, Illinois; COVI-OX T-70, another vitamin E product of Henkel Corporation, La Grange, Illinois; and vitamin E Acetate, a product of Roche Vitamins & Fine Chemicals, Nutley, N.J.

Other types of active ingredients may also be used in Steps 3 and 4 of processes according to the invention such as water-soluble or oil-soluble drugs. Representative examples of some suitable water-soluble drugs which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, and mebendazole.

Representative examples of some suitable oil-soluble drugs which can be used are clonidine, scopolamine, propranolol, estradiol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Not to be excluded, and considered to be included herein as a drug for purposes of the present invention, are antiacne agents such as benzoyl peroxide, triclosan, and tretinoin; antibacterial agents such as chlorohexadiene gluconate; antifungal agents such as miconazole nitrate; anti-inflammatory agents such as salicylic acid; corticosteroidal drugs; non-steroidal anti-inflammatory agents such as diclofenac; antipsoriasis agents such as clobetasol propionate and retinoids; anesthetic agents such as lidocaine; antipruritic agents; antidermatitis agents; and agents generally considered barrier films.

The process is carried out stepwise by combining the ≡SiH containing siloxane(s), the mono-alkenyl polyether, the α-olefin, the α,ω-unsaturated hydrocarbon, the oil, and the platinum catalyst; and mixing these ingredients at room temperature until a gel, elastomer, paste, or emulsion, is formed.

If desired, the gel, elastomer, paste, or emulsion, can be made to include other active or inactive ingredients, or can be further diluted with additional similar or dissimilar oil(s), to form the final composition. A blend of hexane and tetrahydrofuran, a fragrance, or a low molecular weight siloxane, are examples of oils that could be so employed. Waxes such as beeswax and candellila wax can also be employed. Higher temperatures to speed up the process can be used.

If desired, all of the reactants (i.e., the ≡SiH containing siloxane(s), the mono-alkenyl polyether, the α-olefin, the α,ω-unsaturated hydrocarbon, the oil, and the platinum catalyst), can be combined and reacted in one pot. One pot methods are described generally in U.S. Pat. No. 5,889,108 (Mar. 30, 1999), which is assigned to the same assignee as the present invention.

Additional amounts of oil can be added to the gel, i.e., Optional Step 3, and the resulting mixture is subjected to shear force to form the paste. In Step 4, shear force is again used, during or after water is added to the paste, to form a primary emulsion $W_1/O$. The application of shear force is continued in Step 5, where the primary emulsion $W_1/O$ prepared in Step 4 can be formed into a $W_1/O/W_2$ multiple emulsion.

Any type of mixing and shearing equipment may be used to perform these steps such as a batch mixer, planetary mixer, single or multiple screw extruder, dynamic or static mixer, colloid mill, homogenizer, sonolator, or a combination thereof.

Step 3 of the process is an optional step, as noted above. However, when Step 3 is conducted and an oil is included, it should be an oil in which the actve ingredient is soluble. This is particularly important where the active ingredient is a vitamin. Some suitable oils include silicone and hydrocarbon based oils. In addition, the oil should satisfy the melting point and the solubility requirements necessary for end uses being contemplated.

Typically, the process, i.e., Steps 1 and 2, is carried out using approximately a 1:1 equivalent ratio of the ≡Si—H in the ≡Si—H containing siloxane with polyether and higher alkyl groups and the α,ω-unsaturated hydrocarbon. It is expected that useful materials may also be prepared by carrying out the process with an excess of either the ≡Si—H containing siloxane or the α,ω-unsaturated hydrocarbon, but this would be considered a less efficient use of the materials. The remainder of the composition comprises the oil, in amounts generally within the range of about 60–98 percent by weight of the composition.

The most preferred method for preparing compositions according to the invention includes the steps of (i) preparing an elastomeric silicone terpolymer at elevated temperature while mixing; (ii) if required, using an additional oil to solubilize the active ingredient in the case of a vitamin(s), by adding the vitamin(s) to the oil at room temperature while mixing; and (iii) adding the vitamin(s) containing oil slowly to the elastomeric silicone terpolymer at room temperature while mixing.

In particular, a multiple emulsion $W_1/O/W_2$ which is capable of housing fat and water-soluble active ingredients side by side in the inner phases of the emulsion, can be prepared by (i) first producing an inner emulsion, i.e., a primary emulsion $W_1/Q$, and (ii) then adding the inner or primary emulsion $W_1/O$ to the outer aqueous phase $W_2$ using a minimum amount of mixing energy.

In forming a primary emulsion $W_1/O$, it is preferred to use 0.1 to 99 percent by weight of the aqueous phase $W_1$, which amount includes the weight of any water-soluble active ingredient such as a vitamin(s), which may be carried therein. The oil phase 0 of primary emulsion $W_1/O$ is used in an amount of about 1 to 99.9 percent by weight, which amount includes the weight of the elastomeric silicone terpolymer, any other oil, oil-soluble vitamin(s), or fat-soluble active ingredient included therein.

A multiple emulsion $W_1/O/W_2$ can then be prepared by simply mixing together about 0.1 to 70 percent by weight of the primary emulsion $W_1/O$, with about 30 to 99.9 percent by weight of the aqueous final continuous phase $W_2$, which latter amount includes the weight of any additional water-soluble ingredient(s) contained in the final continuous phase.

EXAMPLES

The following examples are set forth in order to illustrate this invention in more detail.

Example 1
Process for Making Elastomeric Silicone Terpolymers

In this example, an ESCO EL-1 processor mixer was employed. The processor mixer was equipped with a one liter jacketed glass container having heating and cooling capability, an anchor sweep blade with speed control settings of 20–300 rpm (2–31 rad/s), a high speed homogenizer with Cowles type blades, speed controls for 750–15,000 rpm (78–1,570 rad/s) operation, a temperature gauge, a product inlet, a vacuum connection, and a circulation bath with heating and cooling capacity. The several starting materials used in preparing elastomeric silicone terpolymers according to this example are listed below.

1. The ≡SiH siloxane was a copolymer generally corresponding to the formula $Me_3SiO(Me_2SiO)_{77}(MeHSiO)_{20}SiMe_3$ in which Me represents methyl. It should be noted that in this copolymer, there are twenty (20) reactive sites available for reaction or crosslinking. Reference may be had to Table 1 below with respect to how the twenty sites were consumed.
2. The α,ω-unsaturated hydrocarbon was 1,5-hexadiene.
3. The mono-alkenyl polyethers had a chain length of 7 and 12, respectively, and were compositions corresponding to the general formulas $CH_2=CH(CH_2)O(CH_2CH_2O)_7H$ and $CH_2=CH(CH_2)O(CH_2CH_2O)_{12}H$.
4. The oil consisted of a cyclic siloxane species decamethylcyclopentasiloxane, i.e., $D_5$.
5. The catalyst was a platinum divinyltetramethyldisiloxane complex containing about one weight percent of platinum carried in a solvent, i.e., Karstedt's catalyst.
6. The post cure quenching agent was a dimethylvinylsiloxy terminated disilloxane of the formula $(CH_3)_2H_2C=CHSiOSiCH=CH_2(CH_3)_2$.
7. The α-olefins were $C_{12}$ and $C_{18}$ α-olefins having the formulas $CH_2=CH(CH_2)_9CH_3$ and $CH_2=CH(CH_2)_{15}CH_3$, respectively.

An elastomeric silicone terpolymer was prepared by adding the ≡SiH siloxane, the mono-alkenyl polyether, and 84–95 percent by weight of $D_5$, to the ESCO EL-1 processor mixer. After loading the materials into the mixer container, the mixer was closed. Heating of the mixer was initiated by setting the circulatory bath set point to about 70° C. The speed of the sweep blade of the mixer was activated to about 25–30 percent of its full capacity, and the speed of the homogenizer of the mixer was activated to about 5 percent of its full capacity. The platinum catalyst was added to the mixer via a syringe inserted through the port hole of the mixer, and the timer was started. Mixing was continued for about 30 minutes. The α-olefin was then added, and mixing of the contents in the container was continued for a minimum of another 15 minutes. Using an analytical balance, the α,ω-unsaturated hydrocarbon, i.e., 1,5-hexadiene, was weighed into a one ounce vial along with 10–20 g of decamethylcyclopentasiloxane ($D_5$), and the vial was capped. The remaining portion of $D_5$ was weighed and placed in a beaker.

Because of the volatility characteristics of 1,5-hexadiene, care was taken when adding it to the reaction mixture. The homogenizer was turned off, and the speed of the scraper was reduced to about 5 percent of its full capacity. The inlet plug of the ESCO processor mixer was removed, and a funnel with an extended stem, was inserted into the port hole of the inlet, so that the stem reached below the surface of the liquid in the container. The α,ω-unsaturated hydrocarbon, i.e., 1,5-hexadiene, was mixed with a portion of decamethylcyclopentasiloxane, and poured into the funnel, followed by the addition of the remaining portion of decamethylcyclopentasiloxane. When the contents in the funnel had been added, the funnel was removed, the inlet was closed, and the timer was restarted.

The speed of the scraper blade was increased to 15–20 percent of its full capacity, and the speed of the homogenizer was increased to 5 percent of its full capacity. The fluid in the mixer container began forming a gel, evidenced by material in the container thickening and climbing up the shaft of the mixer. The time of this occurrence of gelation was noted in a log book, and mixing of the contents was continued. The speeds of both the homogenizer and the scraper were reset to 10–15 percent of their full capacity, depending upon the rigidity of the gel present in the container. The total time of mixing measured from the point of addition of the platinum catalyst was a minimum of 3 hours at a constant temperature of about 70° C. At the end of this time, the set point of the mixer circulatory bath was lowered to 25° C., and mixing was continued. The post cure quenching agent was added, followed by dilution of the contents of the mixer container with decamethylcyclopentasiloxane.

Using the above procedure, three silicone elastomeric terpolymers A, B, and C, were prepared, each having characteristics as shown below in Table 1.

TABLE 1

Terpolymers Prepared in Example 1

| Silicone Elastomeric Terpolymer | Olefin Group | Equivalents of ≡SiH taken up by olefin | Ethylene Oxide Unit | Equivalents of ≡SiH taken up by EO unit | # of Cross Links |
|---|---|---|---|---|---|
| A | $C_{12}$ | 14 | 7 | 1 | 5 |
| B | $C_{18}$ | 13 | 12 | 2 | 5 |
| C | $C_{18}$ | 13 | 7 | 2 | 5 |

As noted previously, the ≡SiH siloxane copolymer used in Example 1, i.e., $Me_3SiO(Me_2SiO)_{77}(MeHSiO)_{20}SiMe_3$, has twenty (20) reactive sites which are available for reaction with sites in other compositions and/or crosslinking with sites in other molecules. In the Table, and using Silicone Elastomeric Terpolymer A as an example, it can be seen that 14 equivalents of the ≡SiH reactive sites in the copolymer were taken up by the olefin portion of the terpolymer, and 1 equivalent of the ≡SiH reactive sites in the copolymer was taken up by the ethylene oxide portion of the terpolymer. The remaining 5 equivalents of the total of 20 equivalents of ≡SiH reactive sites available in the copolymer were taken up in crosslinking with 1,5-hexadiene, which occurred between and among the molecules in forming a gelled three-dimensional network.

Example 2

Preparation of a Water-in-Oil (W/O) Emulsion Containing Mineral Oil & Sunflower Oil 5.0 g of silicone elastomeric terpolymer B prepared in Example 1 were loaded into a glass beaker containing 10.0 g of mineral oil and 10.0 g of sunflower oil. The interfacial tension (IFT) of the sunflower oil used in this example was 19.3 mN/m. The silicone elastomeric terpolymer B and the oils were mixed with a mechanical mixer at 600 rpm (63 rad/s). After 5 minutes of mixing, the addition of water was begun, and 75.0 g of deionized water were added over a 15 minute period using a peristaltic pump. Upon completion of addition of water, the emulsion was mixed for another 5 minutes. A smooth white cream resulted that was stable.

Comparative Example 1

Preparation of a W/O Emulsion Containing Mineral Oil & Sunflower Oil 5.0 g of a solution containing 9 percent by weight of an elastomeric silicone polyether having a 1:5 ratio of (EO)$_{12}$:crosslinks in decamethylcyclopentasiloxane ($D_5$), but not having any higher alkyl containing units in its molecule, were loaded into a glass beaker containing 10.0 g of mineral oil and 10.0 g of sunflower oil. The elastomeric silicone polyether was of the type described in detail in U.S. Pat. No. 5,811,487 (Sep. 22, 1998). The elastomeric silicone polyether and the oils were mixed with a mechanical mixer at 600 rpm (63 rad/s). After 5 minutes of mixing, water addition was begun, and 75.0 g of deionized water were added over a 15 minute period using a peristaltic pump. Upon completion of the water addition, the emulsion was mixed for another 5 minutes. The resulting emulsion was a white cream, but the cream was not stable. This was evidenced by the observation of small drops of a clear liquid, i.e., water, that formed on the surface of the emulsion. This example shows the negative effect of omitting higher alkyl substitutions in elastomeric silicone polymers.

Comparative Example 2

Preparation of a W/O Emulsion Containing Sunflower Oil

Comparative Example 1 was repeated, except that 2.0 g of the elastomeric silicone polyether were used. No mineral oil was added but instead 25.0 g of sunflower oil was used. 73.0 g of deionized water were added over the 15 minute period. It was found that the water and the oil were not completely emulsified. While an emulsion was formed, it was not able to contain all of the oil and water. As a consequence, the oil and the water separated into their own phases. Again, this example shows the negative effect of omitting the higher alkyl substitution in the elastomeric silicone polymer.

Example 3

Preparation of a W/O Emulsion Using Mineral Oil and Arlamol E 5.0 g of silicone elastomeric terpolymer B prepared in Example 1 were loaded into a glass beaker containing 10.0 g of mineral oil and 10.0 g of Arlamol E. The Arlamol E used in this example had an interfacial tension of 4.8 mN/m. Arlamol E is a tradename and a product sold by ICI Surfactants, Wilmington, Delaware. It is a polar organic oil described generally as the polypropylene glycol ether of stearyl alcohol, i.e., polyoxypropylene (15) stearyl ether. The silicone elastomeric terpolymer B, the oil, and the surfactant, were mixed with a mechanical mixer at 600 rpm (63 rad/s). After 5 minutes of mixing, water addition was begun, and 75.0 g of deionized water were added over a 20 minute period using a peristaltic pump. Upon completion of addition of water, the emulsion was mixed for another 5 minutes. The resulting emulsion was a stable smooth white cream.

Example 4
Preparation of a W/O Emulsion Using Arlamol E 5.0 g of silicone elastomeric terpolymer B prepared in Example 1 were weighed into a glass beaker containing 10.0 g of Arlamol E. The silicone elastomeric terpolymer B and Arlamol E were mixed with a mechanical mixer at 600 rpm (63 rad/s). Deionized water was added to the mixture using a peristaltic pump until it appeared that no more water could be emulsified. A total of 58.46 g of deionized water were added over a period of about 15 minutes. The resulting emulsion was stable and white in appearance.

Example 5
Compatibility and Clarity of Silicone Elastomeric Terpolymer with Mineral oil 10.0 g of silicone elastomeric terpolymer B prepared in Example 1 were weighed into a 2 ounce glass vial along with 10.0 g of mineral oil. Silicone elastomeric terpolymer B and mineral oil were stirred by hand and shaken until a uniform mixture had been obtained. A clear liquid resulted. It is noted that, in its neat form, the silicone elastomeric terpolymer B is a translucent white liquid. The addition of mineral oil to the silicone elastomeric terpolymer B in this example had the beneficial effect of rendering the silicone elastomeric terpolymer B more clear.

Example 6
Entrapment of Vitamin A Acetate 50.0 g of the silicone elastomeric terpolymer B prepared in Example 1 were weighed into a glass beaker, and mixed with a mechanical mixer at 400 rpm (42 rad/s) rpm. Vitamin A Acetate, a product of Fluka Chemie AG, Buchs, Switzerland, was added to silicone elastomeric terpolymer B, dropwise with a pipette. Upon it s initial contact with vitamin A acetate, the silicone elastomeric terpolymer B became a clear-yellow liquid. Vitamin A acetate continued to be added to the silicone elastomeric terpolymer B until the degree of clarity decreased, at which point addition of the vitamin was stopped. A total of 13.91 g, i.e., 21.8 percent of the overall weight, of vitamin A acetate were added over a period of about 15 minutes. The resulting material was a slightly hazy yellow liquid.

Example 7
Preparation of a Propylene Glycol-in-Oil Emulsion 50.0 g of the silicone elastomeric terpolymer B prepared in Example 1 were weighed into a glass beaker and mixed at 600 rpm (63 rad/s) with a mechanical mixer. To the beaker, 42.5 g of propylene glycol were added with a pipette over a period of about 15 minutes. The resulting material was a semi-translucent white emulsion.

Example 8
Preparation of a Multiple Emulsion $W_1/O/W_2$,

In this example, two coexisting emulsions were prepared as a final product material. One of the emulsions can be designated $O'/W_2$, while the other emulsion can be designated as the $W_1/O/W_2'$ multiple emulsion.

Part A. Preparation of one of the oil phases (O'). 10 g of stearic acid, a product of Witco Corporation, New York, New York, sold under the tradename HYSTRENE FG, was weighed into a glass beaker, along with 10 g of glycerol monostearate and polyoxyethylene stearate, a nonionic surfactant sold under the tradename ARLACEL 165 by ICI Surfactants, Wilmington, Delaware, and 25 g of petrolatum, a semisolid petroleum jelly used as an emollient, and sold under the tradename WHITE PROTOPET by Witco Corporation, New York, N.Y. The purpose of stearic acid in this example was to act as an anionic surfactant, in addition to the nonionic surfactant ARLACEL 165, in order to emulsify petroleum jelly in the $O'/W_2$ emulsion. As these components are solid, they were placed in a hot water bath at 80° C. in order to melt.

Part B. Preparation of one of the water phases ($W_2$). 50 g of a one percent by weight dispersion containing a crosslinked polyacrylic acid polymer, a thickener otherwise generally known as carbomer, sold under the tradename CARBOPOL EDT 2001, by B. F. Goodrich Company, Brecksville, Ohio, were weighed into another beaker containing 308.5 g of hot deionized water. This beaker was placed in a hot water bath and mixed with a mechanical mixer at 200 rpm (21 rad/s).

Part C. Preparation of the other water phase ($W_2'$). 5.0 g of triethanolamine were weighed into a glass beaker with 50 g of deionized water at 70° C. The solution was mixed by hand using a glass stir rod until it was uniform. The purpose of triethanolamine in this example was to function as a neutralizing agent for the carbomer thickener, which is generally somewhat acidic in nature.

Part D. The primary emulsion ($W_1/O$). The unblended portion of Example 4 was used as the primary emulsion.

When Part A had been uniformly melted, the emulsion $O'/W_2$ was prepared by pouring Part A into Part B, and mixing Parts A and B at 200 rpm (21 rad/s) for 5 minutes. The emulsion $O'/W_2$ was then neutralized with Part C ($W_2'$), and mixed for about five additional minutes. During neutralization, the speed of the mixer was gradually increased from 200 to 350 rpm (21–37 rad/s) to insure adequate mixing. The sample was removed from the hot water bath and allowed to cool to 55° C. while mixing at 350 rpm (37 rad/s). When the temperature of the sample had reached 55° C., 25 g of Part D was added. Mixing was continued, and the sample was allowed to cool to 50° C. After cooling, 1.5 g of DMDM hydantoin and additional deionized water lost due to evaporation, were added to the sample, and it was mixed for 5 minutes.

The resulting material was a smooth white cream in emulsion form that was stable. Examination of the product by optical microscope confirmed the presence and coexistence in the final product of the multiple emulsion $W_1/O/W_2'$. This example demonstrates one practical procedure for making multiple or triple emulsions using elastomeric silicone terpolymers of the invention.

Example 9
Preparation of a Propylene Glycol-in Oil-in Water Multiple Emulsion A hand and body lotion was prep ar ed in this example using the procedure as set forth in Example 8, but with the primary emulsion from Example 7. The resulting material in this example was similar to the hand and body lotion prepared in Example 8, in that it was in the form of a stable smooth white cream.

Example 10A
Preparation of a Water-in-Wax Emulsion

The equipment used in this example included a 250 ml beaker; a Lightning brand LI U08 digital mixer which was equipped with a high shear radial flow impeller having a four blade pitched impeller blade spaced 1 cm from its center; a hot water bath and an oven both set to a temperature of 70° C. The ingredients used to make the emulsion in this example were the silicone elastomeric terpolymer B shown in Table 1, white beeswax, and deionized water. The beeswax and the deionized water were preheated in the oven at 70° C. 10.0 g of beeswax were weighed into the glass beaker along with 5.0 g of the silicone elastomeric terpolymer B. The beaker was placed in th e water bath, and silicone elastomeric terpolymer B and the beeswax were mixed together using the Lightning mixer at about 600 rpm (63 rad/s). Water was then added to the beaker over a period of about 20 minutes using a pipette. The emulsion prepared in this example was a firm white cream which remained stable.

Example 10B
Emulsification of Candelilla Wax

Example 10 A was repeated except that candelilla wax was used instead of beeswax, and the temperature of the hot water bath and the oven were both set at a temperature of 90° C. instead of at 70° C. The material resulting from this example was a hard beige wax.

It should be noted that other types of reactive compositions can be used in preparing elastomeric silicone terpolymers herein without departing from the spirit of the invention.

For example, one can prepare elastomeric silicone terpolymers by reacting the mono-alkenyl polyether and the u.-olefin with the following other types of reactive compositions, instead of using the particular ≡Si—H containing polysiloxanes and α,ω-unsaturated hydrocarbons enumerated above:

$ZMe_2SiO(Me_2SiO)_r(MeHSiO)_sSiMe_2Z$ and
$QMe_2SiO(Me_2SiO)_t(MeQSiO)_uSiMe_2Q$ where Me is methyl; Z is $CH_3$ or H provided there are at least two H atoms per molecule; Q is vinyl or another alpha-unsaturated alkenyl group or $CH_3$ provided there are at least two carbon—carbon double bonds per molecule; r is 0–1,000; s is 0–100; t is 0–1,000; and u is 0–100.

One can also prepare elastomeric silicone terpolymers by reacting the mono-alkenyl polyether and α-olefin with the following types of reactive compositions, instead of using the particular ≡Si—H containing polysiloxanes and α,ω-unsaturated hydrocarbons enumerated above:

$(RMe_2SiO_{1/2})_v(SiO_{4/2})_w(RSiO_{3/2})_x(RMeSiO_{2/2})_y$ and
$QMe_2SiO(Me_2SiO)_z(MeQSiO)_\lambda SiMe_2Q$ where Me is methyl; R is methyl or H provided there are at least two H atoms per molecule; Q is vinyl or another alpha-unsaturated alkenyl group or methyl provided there are at least two carbon—carbon double bonds per molecule; v is 2–50; w is 0–20; x is 0–50; y is 0–1,000; z is 0–1,000; and k is 0–100.

The compositions according to this invention have particular value in the personal care arena. They can be used alone, or blended with other cosmetic ingredients, to form a variety of over-the-counter (OTC) personal care products.

Thus, they are useful as carriers in antiperspirants and deodorants. They are lubricious and can improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss, and provide conditioning benefits.

In cosmetics, they can function as leveling and spreading agents for pigments in make-ups, color cosmetics, foundations, blushes, lipsticks, lip balms, eyeliners, mascaras, oil removers, color cosmetic removers, and powders. When incorporated into sticks, gels, lotions, aerosols, and roll-ons, the compositions can impart a dry, silky-smooth, payout.

In addition, the compositions exhibit other advantageous and beneficial properties such as shelf stability and ease of preparation. Hence, they can have wide application, but especially in antiperspirants, deodorants, skin care products, and for conditioning hair.

Further, the compositions are capable of functioning as carriers for pharmaceuticals, biocides, herbicides, pesticides, and other biologically active substances; and they can be used to incorporate various water and water-soluble substances into hydrophobic systems.

Finally, the compositions have utility as additives for cellulosic or synthetic nonwoven carrier substrates used in wet-like cleansing wipes such as wet-wipes, tissues, and towels, marketed generally for personal hygiene and household cleaning tasks.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A composition comprising an elastomeric silicone terpolymer prepared by a method comprising combining and reacting:

(A) an ≡Si—H containing polysiloxane of the formula $R_3SiO(R'_2SiO)_a(R''HSiO)_bSiR_3$ or the formula $(R'_2SiO)_{a'}(R''HSiO)_{b'}$, and optionally an ≡Si—H containing polysiloxane of the formula $HR_2SiO(R'_2SiO)_cSiR_2H$ or an ≡Si—H containing polysiloxane of the formula $HR_2SiO(R'_2SiO)_a(R''HSiO)_bSiR_2H$, where R, R', and R'' are alkyl groups with 1–6 carbon atoms, a is 0–250, a' is 0–7, b is 1–250, b' is 3–10, and c is 0–250;

(B) a mono-alkenyl polyether of the formula $CH_2=CH(CH_2)_fO(CH_2CH_2O)_g(CH_2CH_3CHO)_hT$, or the formula $CH_2=CH-Q-O(CH_2CH_2O)_g(CH_2CH_3CHO)_hT$, where T is hydrogen, a $C_1-C_{10}$ alkyl group, an aryl group, or a $C_1-C_{20}$ acyl group; Q is a divalent linking group containing unsaturation; f is 0–6, g is 4–100; and h is zero or 1–100;

(C) an α-olefin containing at least ten carbon atoms;

(D) an α,ω-unsaturated hydrocarbon selected from the group consisting of α,ω-dienes of the formula $CH_2=CH(CH_2)_dCH=CH_2$, α,ω-diynes of the formula $CH≡C(CH_2)_eC≡CH$, and α,ω-ene-ynes of the formula $CH_2=CH(CH_2)_eC≡CH$, where d is 1–20 and e is 0–20; and (E) a platinum catalyst; in the presence of (F) an oil selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom;

and allowing the reaction to continue until there is formed a crosslinked three-dimensional gelled network of an elastomeric silicone terpolymer.

2. A composition according to claim 1 in which the oil is a linear volatile methyl siloxane of the formula $(CH_3)_3SiO\{(CH_3)_2SiO\}_k Si(CH_3)_3$ where k is 0–5, or a cyclic volatile methyl siloxane of the formula $\{(CH_3)_2SiO\}_m$ where m is 3–8, the volatile methyl siloxane have a boiling point less than about 250° C. and a viscosity of 0.65–5.0 mm$^2$/s.

3. A material comprising the composition according to claim 1 and an oil, wax, or oil-soluble active ingredient.

4. A material according to claim 3 including mineral oil, sunflower oil, petrolatum, or vitamin A acetate.

5. A material comprising the composition according to claim 1 and a diol or water-soluble active ingredient.

6. A material according to claim 5 including propylene glycol.

7. An emulsion containing the material according to claim 3.

8. An emulsion containing the material according to claim 5.

9. A multiple emulsion containing the material according to claim 3.

10. A multiple emulsion containing the material according to claim 5.

11. A method of treating hair, skin, or underarm comprising applying to the hair, skin, or underarm, the composition according to claim 1.

12. A method of treating cellulosic or synthetic nonwoven carrier substrates comprising applying to cellulosic or synthetic nonwoven carrier substrates the composition according to claim 1.

* * * * *